(12) United States Patent
Foser et al.

(10) Patent No.: US 7,118,085 B2
(45) Date of Patent: Oct. 10, 2006

(54) RETORT SYSTEM

(75) Inventors: Hanspeter Foser, Balzers (LI); Thomas Stampfer, Tosters (AT)

(73) Assignee: Ivoclar Vivadent AG, Schaan (LI)

( * ) Notice: Subject to any disclaimer, the term of this patent is extended or adjusted under 35 U.S.C. 154(b) by 353 days.

(21) Appl. No.: 10/353,275

(22) Filed: Jan. 29, 2003

(65) Prior Publication Data
US 2004/0108610 A1  Jun. 10, 2004

(30) Foreign Application Priority Data
Dec. 6, 2002  (DE) ............... P 102 57 208

(51) Int. Cl.
*A61C 13/20* (2006.01)
(52) U.S. Cl. .............. 249/54; 249/62; 164/244; 164/246; 164/376; 164/DIG. 4
(58) Field of Classification Search ............... 249/54, 249/62; 164/35, 244, 246, 376, DIG. 4
See application file for complete search history.

(56) References Cited

U.S. PATENT DOCUMENTS 3,985,178 A * 10/1976 Cooper .................. 164/237
4,558,841 A * 12/1985 Engelman et al. ............ 249/54
5,406,999 A    4/1995 Berger et al.
5,893,405 A * 4/1999 Berger ..................... 164/244
6,349,758 B1 * 2/2002 Bell ........................ 164/235
6,484,791 B1   11/2002 Vidal
2003/0047299 A1* 3/2003 Ma ........................... 164/376

FOREIGN PATENT DOCUMENTS

| DE | 37 16949 C2 | 12/1988 |
| DE | 198 44 136 A1 | 4/2000 |
| DE | 100 37 352 A1 | 2/2002 |
| EP | 0 438 802 A1 | 7/1991 |

* cited by examiner

*Primary Examiner*—Donald Heckenberg
(74) *Attorney, Agent, or Firm*—John C. Thompson; Alan S. Thompson; Sandra J. Thompson

(57) ABSTRACT

A method for producing dental restoration components includes filling a retort cylinder of a retort system with a forming mass, the retort cylinder being at least partially encircled by a charging body, and hardening the forming mass. After the hardening of the forming mass, the retort cylinder and the charging body are removed from the forming mass, thereby leaving behind a retort. Thereafter, with the assistance of a press blank apparatus, a press blank having an outer contour substantially corresponding to the outer contour of the charging body is pressed into the retort.

14 Claims, 4 Drawing Sheets

RETORT SYSTEM

CROSS-REFERENCE TO RELATED APPLICATIONS

This application claims foreign priority benefits under 35 U.S.C. §119(a)–(d) from German patent application ser. no. P 102 57 208.9 filed Dec. 6, 2002.

TECHNICAL FIELD

The present invention relates to a method for producing dental restoration components, a retort system, and a press blank, all especially for use in connection with dental ovens.

BACKGROUND OF THE INVENTION

Retort ovens have been known for a long time such as, for example, as is disclosed in DE-OS 198 44 136. In retort ovens of this type, a wax model of a dental restoration is embedded in a cast bed in order to produce a negative form. The retort is then heated and warmed so that the model composed of wax melts and there remains the temperature resistant negative form or mold in readiness for the introduction thereinto of a to-be-pressed ceramic mass.

Dental restoration can demand decidedly different forms and volumes. Correspondingly, at the same time several wax models are frequently made ready in a single batch—that is, several wax models are poured within a single retort—and, correspondingly, several ceramic restoration pieces are produced via pressing. The pressing is performed with ceramic mass which is introduced via a feed-in channel and formed into the form mass by a press stamp during simultaneous heating of the negative form.

The mass can be introduced in a pre-pressed condition, in a powder-type condition, or even in a fluid condition, whereby the pre-pressed form body is typically designated as a blank.

Instead of blanks, powder-formed ceramic masses can also be deployed. The use of blanks has, on the one hand, the advantage that an exact or precisely measured amount of ceramic material is deployed so that the operation of the stamp for exerting pressure in the press oven can be exactly specified and can be corrected with a corresponding material offset.

The dental restoration component to be produced can require significantly different amounts of ceramic—either in the form of ceramic powder or in the form of ceramic blanks.

In order to competently handle these requirements, the length of the ceramic blank can be adapted to the requirements, within certain limits. The ceramic blank is introduced into the channel which remains as the negative form of the retort cylinder. In order to achieve a press result of high quality, the ceramic blank must practically be comprised of the same diameter as that of the retort cylinder.

One can, indeed, increase the length of the retort cylinder and, consequently, increase the possible length of the ceramic blank. However, in connection with an overly long length, there arises a comparatively large friction during the press process. This is unfavorable from, for example, the perspective of the adhesion/sliding friction conditions during the press process, which have only been studied to a limited degree and in connection with which there occur pressure oscillations in the hollow space in which the dental restoration is configured.

In order to competently handle various sizes of dental restorations, it has heretofore typically been the practice to maintain a plurality of different retort cylinders in readiness so that, in connection with larger dental restorations of large diameter, larger diameter versions of the retort cylinder can be deployed.

However, maintaining in readiness an inventory of several retort systems of various sizes is a relatively large effort, simply from the point of view of requiring a correspondingly large inventory.

In order to avoid this, it has frequently been the case that an average-sized configuration of a retort system or a retort arrangement is deployed and then several restoration components are stuck outwardly from wax on the growth surface via corresponding support arms, so that the mass is, in total, somewhat enlarged and the blank can be better exploited.

However, imperfect accommodation to the required dental restoration configurations leads to considerable material loss, since, in the case of an only partially pressed blank, the blank must, for all practical purposes, be thrown away.

If, on the other hand, in connection with a desired large material mass, a blank of an overly long length is deployed such that it extends out of the channel of the corresponding retort cylinder, the danger exists that the blank will tip, leading to an unstable press process.

SUMMARY OF THE INVENTION

In contrast to the above-noted shortcomings, the present invention provides a solution to the challenge of providing a retort system, which is an improvement from the point of view of ease of manual manipulation and cost.

In connection with the solution of the present invention, a single retort system can by itself, surprisingly, handle a wider range of ceramic amounts, which are designated for dental restoration models. Via the inventive charging body, a markedly large dental restoration can be created with the same retort system.

In this connection, a correspondingly thicker charging body, which, preferably, encircles the retort cylinder in an annular manner, is deployed. Due to the enlarged thickness, the thus-deployed ceramic blank can, at the same time, be longer without giving rise to a fear that a downgrade in stability will occur.

To this extent, a mass increase to the third power can be realized via the diameter enlargement made possible by the invention so that, as well, a significantly greater mass amount can be achieved with a comparatively thin charging body.

Preferably, the retort cylinder, and the charging body which encircles it, have a round configuration. There then occurs, in connection with the pressing of the ceramic blank, a centralized loading impact on the ceramic blank so that no tipping force is thereby introduced on the blank.

In accordance with the present invention, the charging body can melt, preferably together with the model mass. In this connection, the charging body, as well as the model, can be comprised of wax and can be disposed together with the melted wax of the model in the hollow space of the retort.

In accordance with the present invention, it is particularly advantageous if the charging body comprises a smooth outer surface. Due to the smooth outer surface, it is ensured that an overly strong friction between the hardened form mass and the ceramic blank does not occur, thereby permitting the greatest possible disturbance-free slide friction during the press process.

In accordance with the present invention, it is especially favorable in this connection that the inner top surface of the retort—that is, the outer circumference of the press channel—typically has small wax remnants still remaining thereon. Such wax remnants operate, surprisingly, as lubrication means without, however, forming debris on the dental restoration.

In this connection, it is particularly advantageous that the growth channels, which correspond to the support arms in connection with the wax model securement on the growth surfaces, are configured centrally—that is, clearly within the tube-shaped charging body, so that the outer regions of the ceramic blank do not project into the growth channels or, at the least, do not project into the growth channels at the end of the press process and, in any event, do not project so far as to reach the dental restoration.

It is to be understood that the lubrication effect of the wax remnants endures only so long as the temperature in the retort is not at least substantially over the vaporization temperature of the model mass—that is, this effect lasts during the preparation and pre-heating of the retort oven for the respective actual press process.

In a further particularly favorable configuration, it is provided that the charging body extends over the retort cylinder.

In this configuration, a somewhat longer blank can be deployed as well without engendering any tipping danger.

In furtherance of this purpose, the charging body is disposed on the retort cylinder before the growth on the growth base has begun.

It is to be understood that not only a tube-shaped charging body is contemplated in connection with the term "charging body". In addition, for example, a charging body comprised of several rings axially and/or radially combined with one another can be deployed. It is to be understood that the radial diameter of the charging body can be adapted in any suitable desired manner to the requirements.

The deployment of the inventive charging body or bodies does not rule out the provision, in a conventional manner, of a growth surface, having a blind bore, which can serve as the growth base. If the charging body extends outwardly over this surface, the surface can, in furtherance of this purpose, comprise a corresponding through bore.

Any suitable desired coding system can be deployed to differentiate the various charging bodies from one another. For example, different charging bodies can be differently colored.

If the outer form of the charging body deviates from an annular form, the possibility then also exists that the ceramic blank will be friction-free but, also, that the ceramic blank will be even more securely supported on its side. For example, a six-sided form can be selected in order to achieve the desired outer bracing.

Further advantages, features and details are set forth in the following description of several embodiments of the present invention taken in connection with the figures of the drawings.

DETAILED DESCRIPTION OF THE PREFERRED EMBODIMENT

Figure 1:
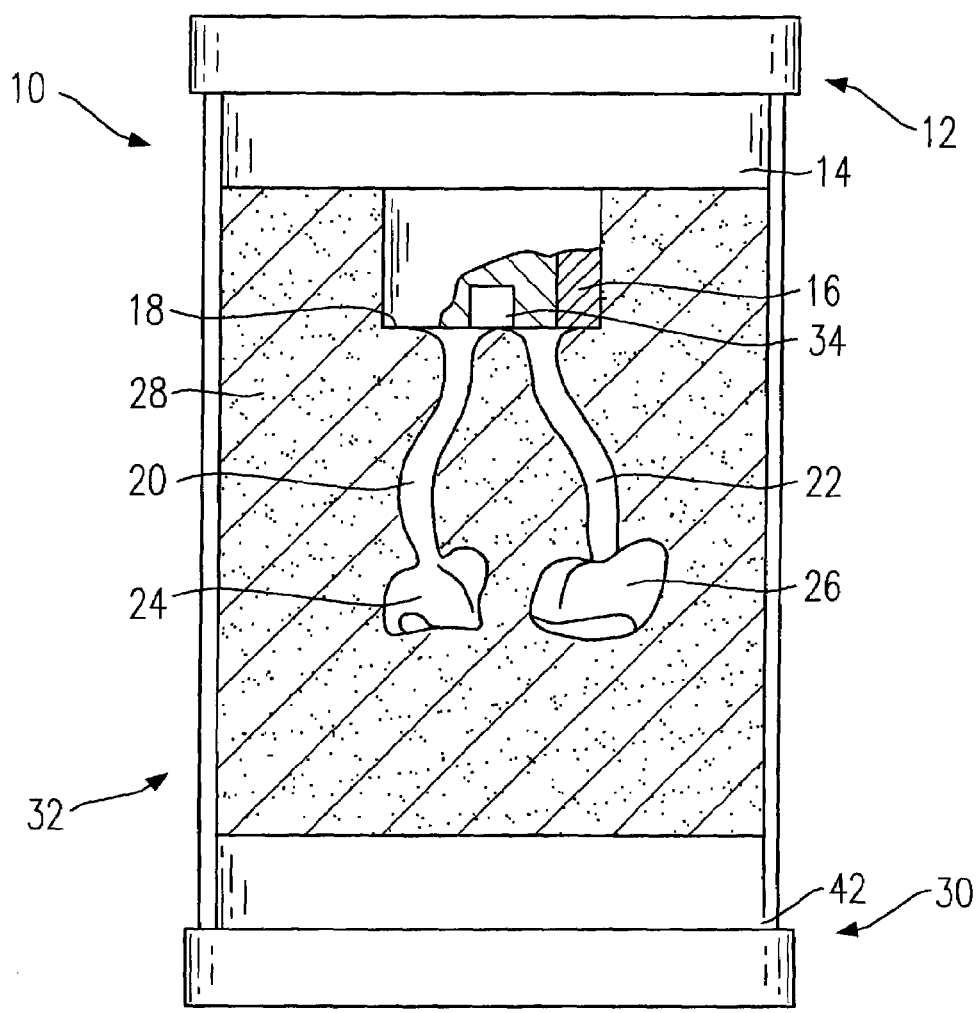
FIG. 1 is a front elevational view, in partial section, of a first embodiment of the inventive retort system.

FIG. 1 shows a first embodiment of the inventive retort system 10 which comprises a retort base 12 from which a retort cylinder 14 extends downwardly, as viewed in the position shown in FIG. 1.

In accordance with the present invention, the side of the retort cylinder 14 is encircled by a charging body 16, whereby, in the illustrated embodiment shown in FIG. 1, the charging body 16 is annularly shaped and has a wall thickness of approximately one-half the radius of the retort cylinder.

The retort cylinder 14 comprises a growth surface 18 on its lower region on the end face thereof turned away from the retort base 12. At least one support arm comprised of wax is mounted on the growth surface 18, whereby, in the illustrated embodiment, two support arms 20 and 22 are configured. Wax models 24 and 26 are provided somewhat centrally in the retort system 10 on the other ends of the support arms 20 and 22, the wax models corresponding in their form to the dental restorations.

In the operational condition shown in FIG. 1, the retort system has already been filled with a forming mass 28 which completely encloses the retort cylinder, the support arms, and the wax models without the presence of any included air.

To effect the filling of the retort system 10, the retort system comprises a retort cover 30 which—as is also the case with the retort base 12—is removable and is in the form of a cylindrical retort form 32, which can be, for example, comprised of a piece of a plastic pipe or can be formed of cardboard. The orientation of the retort system 10 is, in this connection, turned around so that the retort base 12 and the retort cylinder 14 assume the positions shown in FIG. 2. In this operational condition with the retort form 32 removed, the charging body 16 is, initially, inserted or twisted on.

The growth surface 18 comprises, in a conventional manner, a blind hole recess or receptacle 34 which is configured for the receipt of a growth plug or stopper in order that the support arm can be anchored in an improved manner to the growth surface 18. In the illustrated embodiment, the wax models 24 and 26 extend sufficiently outwardly so as to render impossible an insertion of the charging body 16 on the grown out models. It is to be understood that this situation can be remedied, if the models comprise a reduced total outer diameter.

Following the conclusion of the wax working, the retort form 32, which can also be formed of cardboard, is inserted onto an indentation 42 of the retort base 12. Thereafter, the forming mass 28 is carefully introduced. The forming mass hardens into a form mass and is heat resistant with respect to the temperatures which are required for the sintering of ceramic—that is, for example, up to 1100 C.

The retort cover 30, which, in any event, comprises an indentation whose configuration corresponds to that of the indentation 42, is then put on so that the retort system 10 can be manually manipulated as desired.

Figure 2:
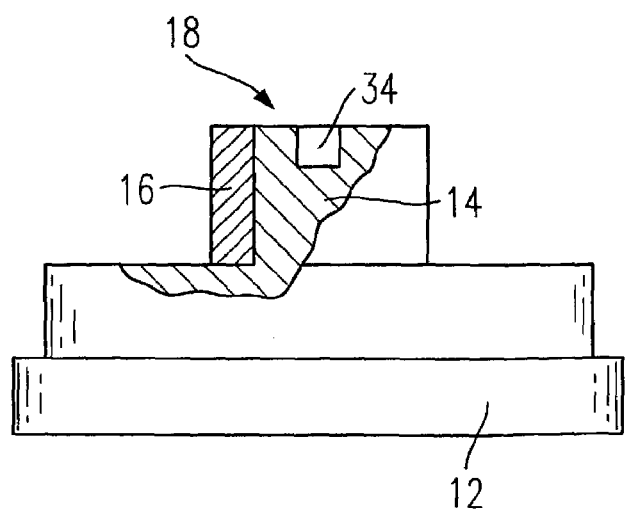
FIG. 2 is a front elevational view, in partial section, of the combination of a retort base and a retort cylinder for the embodiment shown in FIG. 1.

In connection with the preparation of the press, the retort system 10 is then preferably disposed in the position shown in FIG. 2 and the retort base 12, together with the retort cylinder 14 as well as the retort cover 30 and, additionally, the retort form 32, is removed. The forming mass 28 is thereafter somewhat pre-heated so that the charging body 16, the support arms 20 and 22, and, as well, the wax models 24 and 26, melt and exit downwardly. In this condition, the presence of some wax remnants remaining as a fluid film on the walls of the form does not cause any disruption or disturbance.

The forming mass 28 is then again rotated so that it is in the position shown in FIG. 1. In this position, a ceramic blank is introduced which has an outer diameter corresponding to that of the charging body 16. The ceramic blank can have a height/width relation of approximately one to one so that it encloses a significant volume and is suitable for the filling up of large hollow spaces which correspond to that of the wax models 24 and 26 and the support arms 20 and 22. The ceramic blank is, together with the forming mass 28, further heated, whereby the remaining wax remnants are vaporized.

It is important that the wax be handled so as to be residue-free. In this connection, the method of the invention is described, for example, with respect to wax deployed as the material for the charging body 16. It is to be understood, that in lieu of this, other suitable different materials can be deployed which are residue-free—that is, primarily organic materials.

In the embodiment shown in FIG. 2, the charging body 16 is configured as a cylindrical tube which extends over the entire length of the retort cylinder 14—that is, the charging body extends up to the growth surface 18.

It is to be understood that, in lieu of this, other embodiments are possible.

Figure 3:
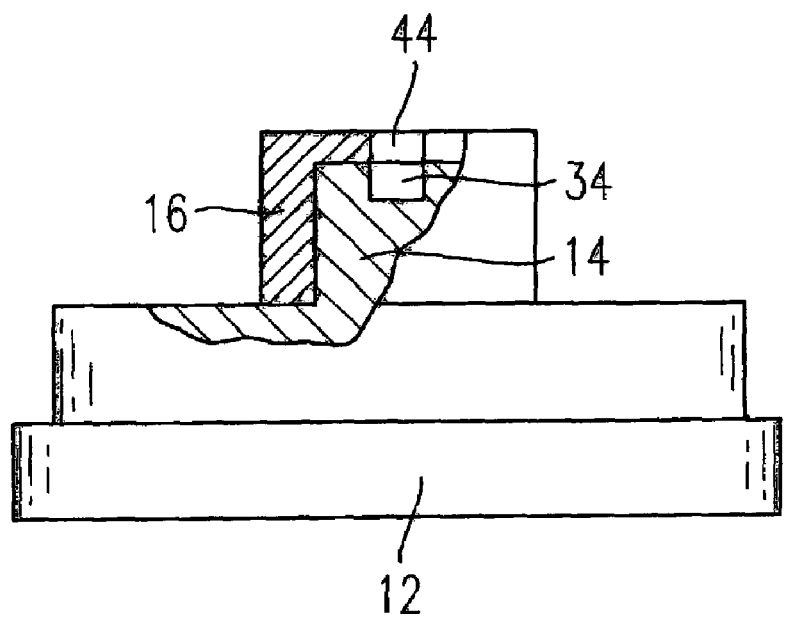
FIG. 3 is a front elevational view, in partial section, of a modified combination of a retort base and a retort cylinder for the embodiment shown in FIGS. 1 and 2.

Thus, in the embodiment shown in FIG. 3, a somewhat enlarged charging body 16 is provided which extends outwardly of the retort cylinder 14 and covers the retort cylinder 14 on its topside (or on its underside in the position shown in FIG. 1). The wall thickness of the charging body 16 on its back surface and on its cylindrical wall are dimensioned the same in this embodiment.

In order that access to the blind hole receptacle 34 is possible, in this configuration, a through receptacle 44 is provided which is aligned with the blind hole receptacle 34 and is securable in the support arms 20 and 22.

Figure 4:
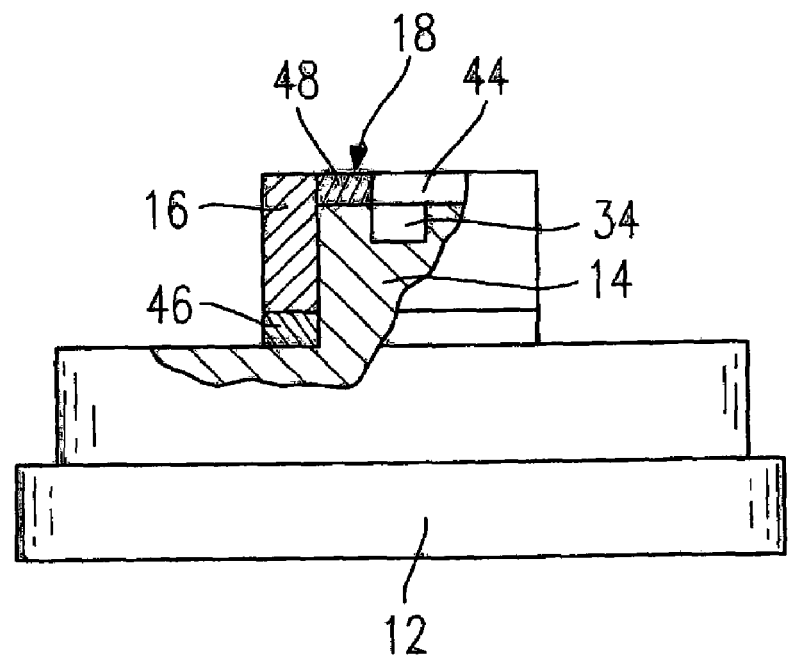
FIG. 4 is a front elevational view, in partial section, of a further modified combination of a retort base and a retort cylinder.

A modified embodiment with a multiple component charging body 16 can be seen in FIG. 4. In this configuration, there is provided a spacer body 46—in the example, a spacer ring 46—which is disposed on the retort base 12 and is releasably inserted on the retort cylinder 14. The spacer body 46 can, together with the retort cylinder 14 and the retort base 12, be removed so that it is not lost if a pre-heating process is to be undertaken.

In this embodiment, in lieu of the pot-shaped charging body 16 as shown in FIG. 3, a ring-shaped charging body 16 can be provided as well. The charging body 16 extends outwardly over the growth surface 18, whereby the ring space between the through receptacle 44 and the charging body 16 is filled via a charging disk 48 which, in correspondence with the required profile, can be configured as a lost or not lost (vaporizable or non-vaporizable) disk.

It is to be understood that, in lieu of the ring-shaped charging body illustrated herein, other suitable desired forms can be deployed for the charging body.

FIGS. 5–8 show different embodiments with the same inner configuration having, however, differing outer forms.

Figure 5:
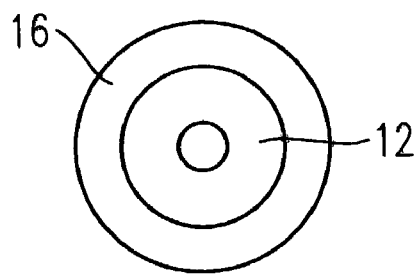
FIGS. 5, 6, 7, and 8 are plan views of respective various embodiments of an inventive charging body.
Figure 6:
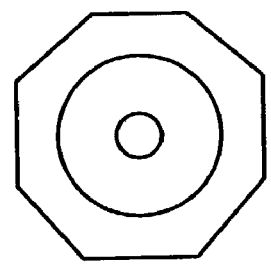
Figure 7:
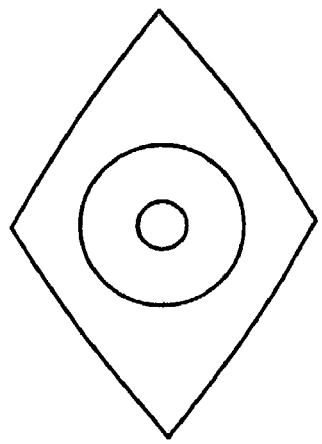
Figure 8:
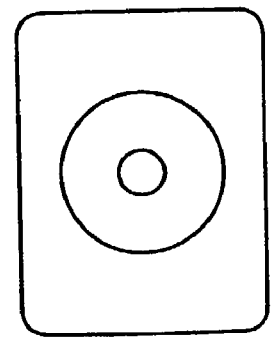

FIG. 5 shows an annular-shaped outer form, FIG. 6 shows an eight-sided outer form, FIG. 7 shows a form comprised of a spherically rounded rhombus, and FIG. 8 shows a right angled-shape with rounded-off corners. Suitable desired forms of the blank can be used, whereby it can be advantageous to permit the blank outer form to deviate from the charging body outer form in order to make possible a reduced contact surface.

Figure 9:
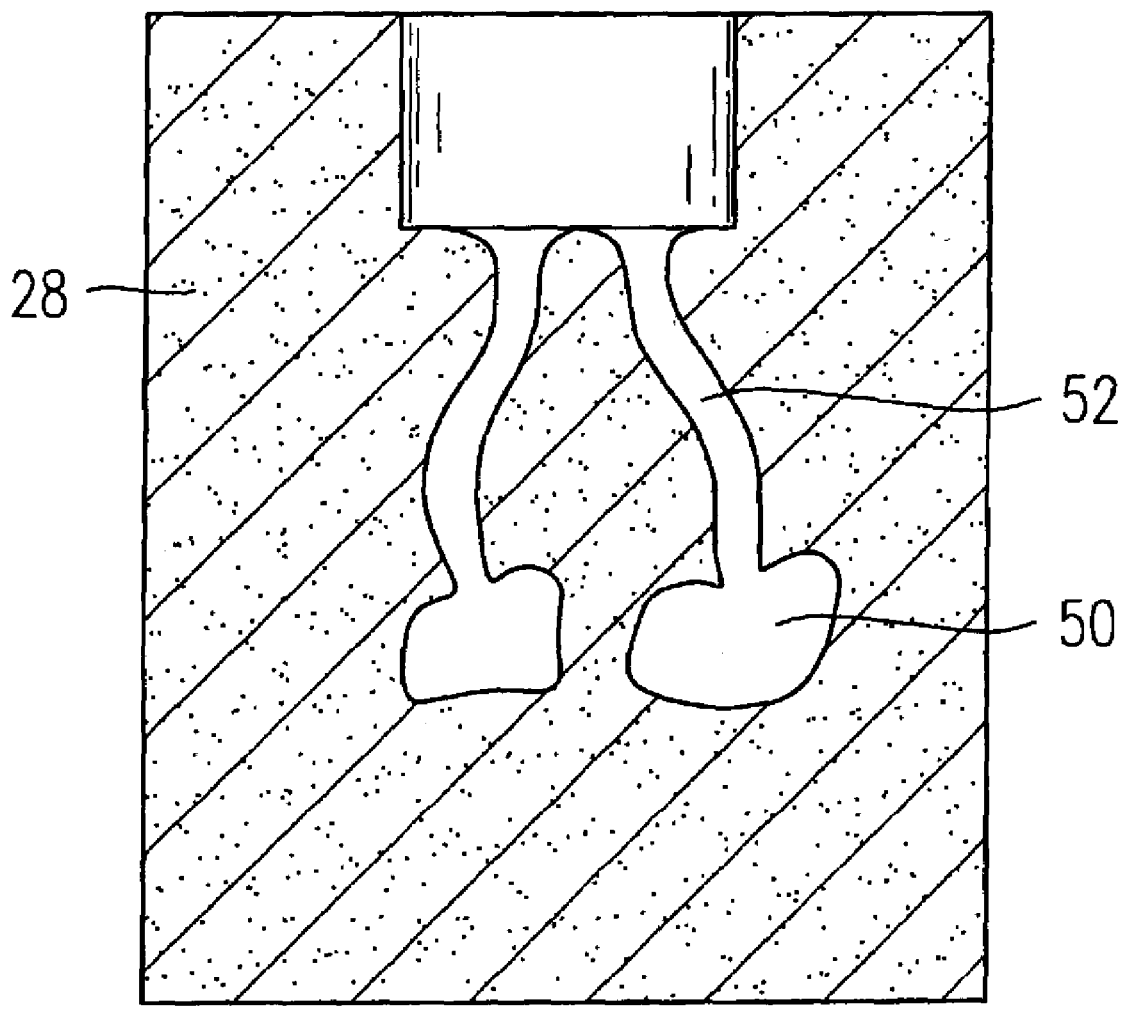
FIG. 9 is a front elevational view, in section, of a press form created in connection with the inventive method.

FIG. 9 shows the configuration of the forming mass 28 which serves as the press form, as soon as the retort base and the retort cylinder are removed and the mass formed of wax has melted. Channels 52 are provided to extend outwardly in lieu of the support arms, and the locations at which the wax models 24 and 26 are configured are provided as hollow spaces 50. The area of the charging body 16 is open so that the ceramic blank can be inserted therein.

It is possible that the charging body 16 as well as the spacer ring 46 and the charging disk 48 can be provided with corresponding coding such as, for example, color coding and/or corresponding text. In this connection, each size can be characterized by a respective color coding so that different sizes can be easily recognized.

The present invention is, of course, in no way restricted to the specific disclosure of the specification and drawings, but also encompasses any modifications within the scope of the appended claims.

What is claimed is:

1. A retort system comprising:
a generally annularly shaped retort cover (30) operable to support a model formed of a mass selected to melt at a melting temperature during a retort preparation process;
a retort base (12) including a retort cylinder (14); and
a charging body (16) at least partially encircling the retort cylinder (14), the charging body being formed of a mass selected to melt during the retort preparation process, and further comprising a spacer body (46) disposed between the charging body (16) and the retort cylinder (14), the spacer body being meltable at a melting condition corresponding to that of the melting condition of the charging body (16).

2. A retort system according to claim 1, wherein the spacer body (46) has an outer contour substantially corresponding to that of the charging body (16).

3. A retort system according to claim 1 and further comprising a charging disk (48) corresponding to the inner contour of the charging body (16) mounted on an end face of the retort cylinder (14) and having a wall thickness corresponding to that of the spacer body (46).

4. A retort system comprising:
a generally annularly shaped retort cover (30) operable to support a model formed of a mass selected to melt at a melting temperature during a retort preparation process;
a retort base (12) including a retort cylinder (14); and
a charging body (16) at least partially encircling the retort cylinder (14), the charging body being formed of a mass selected to melt during the retort preparation process and further comprising a spacer body (46) for maintaining the space between the charging body (16) and the retort base (12), and a coding indicia associated with the spacer body (46) indicating via color indicia, information concerning an aspect of the spacer body (46) differentiating the spacer body (46) from other spacer bodies (46) including at least one of the predetermined length and the predetermined outer diameter of the spacer component.

5. A retort system according to claim 4, wherein the spacer body (46), the retort base (12), and the retort cylinder (14) are removable from the hardened forming mass.

6. A retort system according to claim 5, wherein at least a portion of the charging body (16) is in the form of a tube.

7. A retort system according to claim 5, wherein the charging body (16) includes a floor extending in at least partial coverage over an end face of the retort cylinder (14).

8. A retort system according to claim 5 and further comprising at least one of a blind hole receptacle (34) formed on an end face of the retort cylinder (14) and a through receptacle (44) formed on a selected one of a charging disk and the charging body (16).

9. A retort system according to claim 1, wherein the charging body (16) includes a coding indicia indicating via color indicia, that the charging body has one of the respective wall thicknesses of a range of particular charging bodies suitable for use with the same respective retort cylinder (14).

10. A retort system according to claim 5, wherein the charging body (16) is annularly shaped.

11. A retort system according to claim 5, wherein the charging body (16) is configured as a pre-finished wax piece whose melting point substantially corresponds to the melting point of wax models (24, 26) of a dental restoration.

12. A retort system according to claim 1 wherein different charging bodies (16) and/or different spacer bodies (46) and/or different charging disks (48) can be inserted onto the retort cylinder (14).

13. A retort system according to claim 4, wherein the charging bodies (16) and/or spacer bodies (46) and/or the charging disks (48) comprise a coding indicia.

14. A retort system according to claim 13 wherein the coding indicia is a color indicia.

* * * * *